United States Patent [19]

Keith et al.

[11] 4,438,139

[45] * Mar. 20, 1981

[54] POLYMERIC DIFFUSION MATRIX CONTAINING ESTROGENS

[75] Inventors: Alec D. Keith, Miami, Fla.; Wallace Snipes, State College, Pa.

[73] Assignee: Key Pharmaceuticals, Inc., Miami, Fla.

[*] Notice: The portion of the term of this patent subsequent to Sep. 22, 1998 has been disclaimed.

[21] Appl. No.: 439,023

[22] Filed: Jan. 4, 1982

Related U.S. Application Data

[63] Continuation of Ser. No. 281,391, Jul. 8, 1981, abandoned, which is a continuation-in-part of Ser. No. 217,400, Dec. 17, 1980, Pat. No. 4,321,252, and Ser. No. 167,729, Jul. 11, 1980, Pat. No. 4,291,014, and Ser. No. 109,242, Jan. 3, 1980, abandoned, which is a continuation-in-part of Ser. No. 2,565, Jan. 11, 1979, abandoned.

[51] Int. Cl.³ .................... A61L 15/03; A61K 31/79; A61K 31/74

[52] U.S. Cl. ........................ 424/28; 424/78; 424/80

[58] Field of Search ............... 424/28, 78, 80

[56] References Cited

U.S. PATENT DOCUMENTS

| | | | |
|---|---|---|---|
| 2,127,896 | 10/1938 | Vohrer | 18/55 |
| 2,138,751 | 11/1938 | Vohrer | 18/54 |
| 2,155,658 | 4/1939 | Herrmann et al. | 424/78 |
| 2,160,503 | 5/1939 | Herrmann | 424/78 |
| 2,340,866 | 2/1944 | Dangelmajor | 260/8 |
| 2,491,642 | 12/1947 | Brant | 264/213 |
| 2,693,438 | 11/1954 | Ward | 424/28 |
| 3,287,222 | 11/1966 | Larde et al. | 424/28 |
| 4,210,633 | 7/1980 | Takruri et al. | 424/28 |
| 4,291,014 | 9/1981 | Keith et al. | 424/28 |
| 4,321,252 | 3/1982 | Keith et al. | 424/28 |

FOREIGN PATENT DOCUMENTS

| | | |
|---|---|---|
| 1505318 | 12/1967 | France . |
| 2245161 | 4/1975 | France . |
| 48-92522 | 11/1973 | Japan . |
| 49-30525 | 3/1974 | Japan . |
| 49-45952 | 5/1974 | Japan . |
| 49-48728 | 12/1974 | Japan . |
| 51-112511 | 3/1975 | Japan . |
| 50-56385 | 5/1975 | Japan . |
| 52-38016 | 3/1977 | Japan . |
| 53-50320 | 5/1978 | Japan . |
| 933668 | 8/1963 | United Kingdom ............... 424/78 |
| 219116 | 3/1973 | U.S.S.R. . |

OTHER PUBLICATIONS

Peierls Modern Plastics 18: 53–56, Feb. 1941, Polyvinyl Alcohol Plastics.
Hess et al., Rubber Age 53: 431–433, Aug. 1943, Molding Polyvinyl Alcohol.
Ita et al., Bulletin Pharm. Research Inst., Osaka Medical College (2) 1-3, (1951) II, "On a New Water-Soluble Ointment".
Hirai Bull. Inst. Chem. Koyoto Univ. 33: 21–37, (1955), The Gel-Elasticity of High Polymers.
Langhammer et al., Naturwissen Schaften 43: 125–126, (1956) (PVP-PVA).
(PVP-PVA) Nehring Plaste und Kautschuk 3: 279–280, (1956).
Ward et al., Amer. Perf. & Cosmetics 79: 52–55, Nov. 1964, The Use of Polyvinyl Alcohol in Film-Forming Bases.
Ward et al., J. Soc. Cos. Chem. 15: 327–335, (1964), Cosmetic Applications of Polyvinyl Alcohol.
Toydshima, K., "Compatibility of Polyvinyl Alcohol with Other Water-Soluble High Polymers", in Finch et al. Ed. (1967?), Polyvinyl Alcohol: Properties & Applications, 535–553.
Ban et al., Pharmazie 29 H9: 597–602, (1974) (PVP-PVA).
Nagy et al., "Formation of Disperse Structures in Polymer Gels", Proc. Int. Conf. Colloid & Surface Science, Budapest Hungary, Sep. 1975, Wolfram et al., pp. 447–453.

*Primary Examiner*—Shep K. Rose
*Attorney, Agent, or Firm*—Wegner & Bretschneider

[57] ABSTRACT

A polymeric diffusion matrix for the sustained release, intravaginal administration of an estrogen is provided. The matrix consists of polyvinylalcohol, polyvinylpyrrolidone and a polar plasticizer.

13 Claims, No Drawings

POLYMERIC DIFFUSION MATRIX CONTAINING ESTROGENS

This application is a continuation application of U.S. application Ser. No. 281,391, filed July 8, 1981, now abandoned, which in turn is a continuation-in-part of U.S. application Ser. No. 217,400, filed Dec. 17, 1980, now U.S. Pat. No. 4,321,252, U.S. application Ser. No. 167,729, filed July 11, 1980, now U.S. Pat. No. 4,291,014, and U.S. application Ser. No. 109,242, filed Jan. 3, 1980, now abandoned, the last of which is a continuation-in-part of U.S. application Ser. No. 2,565, filed Jan. 11, 1979, now abandoned.

SUMMARY OF THE INVENTION

The present invention relates to a polymeric diffusion matrix containing estrogens. More particularly, the invention relates to a polymeric diffusion matrix containing an estrogen characterized by a sustained release of the estrogen. For the purposes of this application, the term "estrogen" includes estrone, estradiol, estriol and esters and other pharmacologically effective derivatives of each, such as estrone benzoate, estradiol diacetate, estradiol 3-benzoate and estradiol 3-valerate, as well as compounds chemically related to estrone, estradiol and estriol which exhibit estrogen-like physiological effects.

A self-supporting polymeric diffusion matrix is provided for the sustained release of estrogen in order to deliver said estrogen to a patient and provide said patient with a uterine wall maintenance effect, said matrix comprising from about 1 to about 60% by weight of a polar plasticizer; from about 6 to about 30% by weight polyvinylalcohol; from about 2 to about 30% by weight polyvinylpyrrolidone; and a pharmaceutically effective amount of estrogen to provide a sustained release of said estrogen over a prolonged period.

Polar plasticizers suitable for use in this invention includes principally poly-loweralkylene oxides, but other polar plasticizers such as diethylphthalic diethylphthalate may be used.

In one embodiment the polar plasticizer is glycerol present in an amount of from about 2 to about 60% by weight. In another embodiment the polar plasticizer is polyethylene glycol present in an amount of from about 1 to about 15% by weight. A still further embodiment contemplates a mixture of glycerol and polyethylene glycol wherein the latter is present in an amount by weight of from about 1 to about 5 parts per weight glycerol.

The self-supporting polymeric diffusion matrix generally contains a mixture of polyvinylalcohol and polyvinylpyrrolidone, although it will be understood that other polymeric mixtures may be used provided they yield the desired sustained release effect. For example, both the polyvinylalcohol and the polyvinylpyrrolidone may be partially or completely replaced with from about 1 to about 9% agar or agarose, and preferably from about 1.5 to 3% agar or agarose, 2% agar or agarose being particularly preferred.

As the polyvinylalcohol used in the present invention, there is generally contemplated one having a molecular weight from about 50,000 to about 150,000, and more preferably about 100,000 to about 150,000, 115,000 having been used in related systems of the present inventors with success. The polyvinylalcohol should be hydrolyzed, generally at least to the extent of 90% with a preferred embodiment being at least 95% hydrolyzed. The polyvinylpyrrolidone should have a molecular weight of from about 15,000 to about 85,000, and more preferably from about 20,000 to about 60,000. Polyvinylpyrrolidone with a molecular weight of 40,000 is a particularly preferred embodiment.

The amount by weight of the ingredients other than the polar plasticizer generally should be in the following ranges: Polyvinylalcohol is generally present in an amount of from about 6 to about 30% by weight, with 20% being a preferred embodiment; polyvinylpyrrolidone is present generally in an amount of from about 2 to about 30% by weight, with about 10% being preferred.

In particular embodiments of this invention the total amount of polyvinylalcohol and polyvinylpyrrolidone used is from about 25% to about 50% by weight.

The water-soluble polymer can be replaced with (in addition to agar) gum arabic, gum tragacanth, polyacrylic acid, polymethacrylic acid, polyvinyloxazolidone, polyvinylmorpholinone, and polyvinylpiperidone.

Polyalkylene glycols (poly-loweralkylene oxides) such as polyethylene glycol and polypropylene glycol may replace all or part of the glycerol.

The estrogens suitable for use in this invention provide a source of pharmacologically active estrone, estradiol or estriol in the bloodstream. We have found that more than one such estrogen may be administered simultaneously to provide a high flux of physiologically active estrogen. The particular derivatives to be chosen for simultaneous administration must be ones that will not interfere with each other's solubility and permeability characteristics. It is also contemplated that the matrix in accordance with this invention contain sufficient progesterone to produce blood progestersone levels of about 2–10 ng/ml. It has been suggested that the administration of progesterone simultaneously with estrogens will mitigate the reported carcinogenic properties of estrogens.

In forming the matrix, excess water is not required. In accordance with a preferred aspect of the present invention, about 2% by weight estradiol source is included in the diffusion matrix. The resultant homogenous mixture is poured into forms preferably made of glass or stainless steel. For transdermal application a diffusion matrix with a thickness of about 1 to about 3 mm is in accordance with a preferred aspect of this invention. This diffusion matrix can be cut to obtain the desired surface area once it is suitably cured. In accordance with another preferred aspect of this invention the homogenous mixture is poured into oval or other suitably shaped forms of 1 cm average thickness, the overall dimensions of which are suitable to produce geometries acceptable for insertion into the vaginal canal for delivery of the drug in the vicinity of the cervix. The particular geometry chosen will allow the finished product to stay in place yet be easily removable manually. Such geometries as T-shaped, Y-shaped, golf tee shaped or cervical ring may be appropriate.

The following methods may be used for preparing the diffusion matrix of the present invention.

In one method, the matrix is formed at atmospheric pressure. Water and polar plasticizer are first mixed together. A polar plasticizer such as glycerol or polyethylene glycerol component in the matrix. A matrix formed without a polar plasticizer is not flexible and has poor diffusional contact with the skin, causing unreliable diffusion release. The polyvinylalcohol and polyvinylpyrrolidone are then added to the polar plasticizer water mixture at room temperature with agitation. The mixture is heated to a temperature within the range of from 90° to about 95° C. at atmospheric pressure to extend the polymers. If desired the mixture may be maintained at an elevated temperature for a period of time, based on polymer stability, prior to addition of the drug. Thus, the mixture is stable for a period of time and may be kept for such a period before being mixed with the drug to be delivered to the patient. Thereafter, the mixture is temperature-adjusted and the drug to be applied to the patient is then added to the mixture, with thorough agitation. Once a homogenous mixture of the polymer solution and drug is obtained, the mixture is ready to be cast to form in a drug-containing diffusion matrix. After casting the mixture is cooled to a temperature such that gelaton occurs.

In another method, the polymeric material is heated under pressure to accomplish dissolution in the mixture, the desired estrogen or estrogens are mixed in and the material is extruded under pressure into a mold of suitable size and geometry. The use of pressure allows for the incorporation of higher amounts of polymeric material into the matrix, thus improving film strength and dimensional stability and allowing for thinner matrices. This pressure method further reduces or eliminates altogether curing and/or drying time.

It has been further found that curing is facilitated by subjecting the matrix to a temperature down to about −20° C. immediately after casting, especially when polyethylene glycol is used as the plasticizer. The setting time is quickened considerably.

Sodium dodecyl sulfate or sorbitan (Tween-20) or other detergents may be added in an amount of 0.1 to 10% by weight, based on the matrix, as a dispersing agent, if desired. Soy phosphatides may be added as estrogen solubilizing agents in a concentration of 0.1-10% by weight. An absorption facilitator to insure skin penetration such as dimethylsulfoxide, decylmethylculffoxide, or other penetration enhancers may also be added. Suitable preservatives, such as sodium benzoate, may be also added where indicated.

The present drug delivery device comprises the drug-containing diffusion matrix which can either be inserted into the vagina in the form of a self supporting vaginal insert or applied as a transdermal patch with means for fastening the matrix to the skin of a patient. Such means can take various forms, such as an occlusive backing layer forming a kind of "bandage" with the diffusion matrix being held against the skin of a patient being treated. A polyethylene or Mylar tape is contemplated as one form of occlusive layer in accordance with the present invention. It can also take the form of an elastic band, such as a cloth band, a rubbery band or other material. Here, the diffusion matrix is placed directly on the skin and held in place over the arm or wrist of the patient. An intermediate adhesive layer between the diffusion matrix and the skin capable of permitting the transdermal application of the drug can also be used.

The invention is illustrated by the following non-limiting examples.

EXAMPLE I

Together there are mixed 20 gm glycerol and 55 ml water. This mixture is heated to 90° C.; after reaching at least 70° C., there are slowly added 15 gm polyvinylalcohol (PVA 100% hydrolyzed, molecular weight 115,000) and 8 gm polyvinylpyrrolidone (mw 40,000). The mixture is stirred at 90° C. until solution is effected, which may take about 10 minutes; it will be appreciated that with larger quantities, a considerably longer period of time may be needed. 98 ml of this solution is then mixed with 2 gm estradiol 3-benzoate, this mixture then being mechanically stirred until homogeneous. The homogeneous mixture is then poured into forms made of glass or stainless steel which serve as templates to produce a diffusion matrix having a thickness of about 0.2 to 2 mm. This diffusion matrix is then cut into square pieces of about 1 inch on each side, i.e., to provide a total surface area of about 6.5 cm$^2$.

The diffusion matrix is applied to the skin of a patient in need of uterine wall maintenance, the estradiol 3-benzoate being transdermally delivered. The diffusion matrix is ideally applied to the skin of the patient by means of a single-piece bandage having the diffusion matrix in the center under the occlusive layer, the bandage being provided to the patient with a peel-off cover much like a "band-aid".

EXAMPLE II

Instead of casting the fluid homogenous drug containing matrix with a 2 to 2 mm thickness as disclosed in Example I, it is poured into oval forms 1 cm thick. The cured diffusion matrix is applied in the form of a vaginal insert into a patient in need of uterine wall maintenance, the estradiol 3-benzoate being delivered in the vicinity of the cervix of the patient.

EXAMPLE III

In place of the glycerol of Example I, there is substituted 10 gm polyethylene glycol having a molecular weight of 1000 and 10 ml water. The resultant diffusion matrix is more rigid than that of Example 1, thus improving its ease of application in the form of a vaginal insert.

EXAMPLE V

In place of the polyvinylalcohol and polyvinylpyrrolidine of Example I, there are substituted 2 gm agarose and 21 ml water, yielding a diffusion matrix for the delivery of estradiol 3-benzoate.

EXAMPLE VI

The following mixture, listed in parts by weight, is heated under pressure, about 3 atmospheres being suitable, to 110°-130° C.:

| Polyvinylalcohol | 20 parts | (115,000 m.w.) |
| --- | --- | --- |
| Polyvinylpyrrolidone | 15 parts | (40,000 m.w.) |
| PEG 4000 | 5 parts | (4,000 m.w.) |
| Glycerol | 3 parts | |
| Estradiol | 2 parts | |
| Water | to 100 parts | |

This mixture is first prepared by heating polyvinylalcohol and water to effect dissolution. The PEG 4000, polyvinylpyrrolidone and glycerol are dissolved in cold water, and the two aqueous mixtures are brought together under heat and pressure as described above. Finely divided estradiol or other estrogen is rapidly mixed into the viscous liquid and the mixture is extruded into the appropriate mold for producing vaginal inserts.

EXAMPLE VII

In place of the PEG 4000 of Example VI, PEG 1000 is used in the mixture to form vaginal inserts.

While the above Examples have used estradiol and estradiol 3-benzoate the estrogen, it must be understood that other estrogens are administered in exactly ths same fashion. This invention is not, therefore, limited to the particular estrogens disclosed herein, but provides a suitable vehicle for the administration of estrogens of any pharmacologically active type small enough to pass through the skin.

What is claimed is:

1. A self-supporting polymeric diffusion matrix for the sustained release of a pharmacologically acceptable estrogen in order to deliver said estrogen to a patient and provide said patient with a uterine wall maintenance effect, said matrix comprising from about 1 to about 60% of a polar plasticizer, from about 6 to about 30% by weight polyvinylalcohol, from about 2 to about 30% by weight polyvinylpyrrolidone, and a pharmaceutically effective amount of the estrogen to provide a sustained release of said estrogen over a prolonged period.

2. The polymeric diffusion matrix of claim 1, wherein the total content of polyvinylalcohol and polyvinylpyrrolidone is from about 25% to about 50% by weight, based on the weight of the matrix.

3. The polymeric diffusion matrix of claim 1 wherein said polar plasticizer is glycerol.

4. The polymeric diffusion matrix of claim 3 wherein said polyvinylalcohol has a molecular weight of about 50,000 to about 150,000.

5. The polymeric diffusion of claim 3 wherein said polyvinylalcohol has a molecular weight of about 100,000 to about 150,000.

6. The polymeric diffusion matrix of claim 3 wherein said polyvinylpyrrolidone has a molecular weight of from about 15,000 to about 85,000.

7. The polymeric diffusion matrix of claim 3 wherein said polyvinylpyrrolidone has a molecular weight of about 20,000 to about 60,000.

8. The polymeric diffusion matrix of claim 1 wherein said polar plasticizer is polyethylene glycol present in an amount of about 1 to about 15% weight.

9. The polymeric diffusion matrix of claim 1 wherein said polar plasticizer is a mixture of glycerol and polyethylene glycol wherein said polyethylene glycol is present in an amount by weight of from about 1 to 5 parts per weight glycerol.

10. The polymeric diffusion matrix of claim 1, wherein the estrogen is selected from the group consisting of estrone, estradiol, estriol and their pharmaceutically acceptable esters and derivatives.

11. The polymeric diffusion matrix of claim 10, wherein the estrogen is estradiol 3-benzoate, estradiol 3-valerate or estradiol diacetate.

12. The polymeric diffusion matrix of claim 1, further comprising a pharmocologically effective amount of progesterone.

13. The polymeric diffusion matrix of claim 1, comprising about 20% by weight polyvinylalcohol of molecular weight about 115,000, about 15% by weight of polyvinylpyrrolidone of molecular weight about 40,000, about 5% by weight polyethyleneglycol of molecular weight about 4000 and about 3% by weight glycerol.

* * * * *